United States Patent [19]

Weissman

[11] 4,321,036

[45] * Mar. 23, 1982

[54] PROSTHODONTIC DOWEL PIN

[75] Inventor: Bernard Weissman, New York, N.Y.

[73] Assignee: Ipco Corporation, White Plains, N.Y.

[*] Notice: The portion of the term of this patent subsequent to May 27, 1997, has been disclaimed.

[21] Appl. No.: 121,833

[22] Filed: Feb. 15, 1980

Related U.S. Application Data

[63] Continuation-in-part of Ser. No. 903,744, May 8, 1978, Pat. No. 4,205,443.

[51] Int. Cl.$^3$ .............................................. A61C 19/00
[52] U.S. Cl. ...................................... 433/74; 433/141
[58] Field of Search ............... 433/74, 53, 213; 81/71; 29/282

[56] References Cited

U.S. PATENT DOCUMENTS

| | | | |
|---|---|---|---|
| 328,837 | 10/1885 | Case | 433/221 |
| 640,551 | 1/1900 | Fones | 433/221 |
| 1,213,587 | 1/1917 | Chester | 433/221 |
| 1,279,805 | 9/1918 | Whitaker | 433/194 |
| 1,780,117 | 10/1930 | Craigo | 433/74 |
| 4,001,938 | 1/1977 | Cooper | 433/74 |
| 4,127,939 | 12/1978 | Samuel et al. | 433/74 |
| 4,205,443 | 6/1980 | Weissman | 433/74 |

FOREIGN PATENT DOCUMENTS 2515445 10/1976 Fed. Rep. of Germany ........ 433/74

Primary Examiner—Robert Peshock
Assistant Examiner—John J. Wilson
Attorney, Agent, or Firm—Friedman, Goodman & Teitelbaum

[57] ABSTRACT

A dowel pin for removably mounting a dental model cast relative to a base cast. The dowel pin includes a head portion and a shank portion axially extending therefrom. The head portion is adapted to be fixedly secured in the dental model cast and the shank portion is adapted to be removably insertable into a complementary opening in the base cast. The head portion includes an externally threaded male member axially extending therefrom with a collar surrounding the base of the male member. The outer diameter of the collar proximates the diameter of the shank portion so that it can enter into the opening in the base cast. The shank portion has an internally disposed complementary thread which receives the male member therein. A tool is provided for engaging a free end of the shank portion in order to both thread and unthread the shank portion to and from the head portion, so that the dental model cast or segments thereof can easily be replaced and removed from the base cast. Preferably, another tool is provided for extracting the shank portion from the opening in the base cast after it has been disengaged from the head portion.

11 Claims, 17 Drawing Figures

PROSTHODONTIC DOWEL PIN

RELATIONSHIP TO OTHER APPLICATIONS

This application is a continuation in part of U.S. Ser. No. 903,744 filed May 8, 1978, and now U.S. Pat. No. 4,205,443, for a "Two-Part Dowel Pin And Tool Therefor" by the applicant of the present invention. The material therein is herein incorporated by reference.

BACKGROUND OF THE INVENTION

This invention relates to dentistry, and more particularly to a two-part dowel pin for prosthodontic casts, as well as tools for use therewith.

In making models of a patient's teeth, it is common practice to first form a negative impression of the teeth. Dowel pins are positioned in the center of the impressions of particular teeth which are to be worked on. The negative impressions of the teeth are then filed with a die material to form a positive replica or die of the teeth.

In the formation of such dental models, the dental model cast is situated on a base cast. The dowel pins are utilized for positioning the dental model cast on the base cast. Numerous manipulations take place on the dental model cast and it is accordingly required to frequently insert and remove the dental model cast from the base cast.

In the prior art, it was common practice to utilize one piece dental pins. Such pins had numerous shapes and arrangements. For example, in applicant's own U.S. Pat. Nos. 3,875,665 and 3,932,939, dowel pins are disclosed of such one piece construction. In the latter patent, two pins are utilized, one as a locating pin and one as an aligning pin between the dental model cast and the base cast. Other shapes of dowel pins are described in U.S. Pat. No. 3,286,385 where the dowel pin is utilized in conjunction with a clip inserted in the base cast which provides a spring-like retention on the dowel pin. A pin and sleeve combination is described in U.S. Pat. No. 3,518,761 to facilitate insertion and removal of the dowel pin from a sleeve which is inserted in the base cast. A further shaped dowel pin is described in U.S. Pat. No. 1,279,805.

All of these, however, utilize a one piece construction which presents problems in the insertion and removal thereof. Frequently, the pin can become bent or damaged during continuous utilization and appropriate positioning of the dental model cast on the base cast become displaced.

In the aforementioned parent application, there is described a two part dowel pin for removably mounting a dental model cast relative to the base cast. The dowel pin includes a head portion and a shank portion extending therefrom. The head portion is adapted to be fixedly secured into the dental model cast so that the exposed end thereof is flush with a flat surface of the dental model cast. The shank portion is adapted to be removably inserted into a complementary opening provided in the base cast. Preferably, a sleeve member is provided in the opening to slidably receive the shank portion therein. Threads are provided on a male member extending from the shank portion which are received in a correspondingly threaded female portion formed within the head portion.

In the aforementioned parent application, the shank portion is provided with a vertical flat surface longitudinally extending from the free end thereof opposite the end of the shank portion having the threaded member. The vertical flat surface extends outwardly from the base cast and is engaged by a tool for rotating the shank to disengage the shank portion from the head portion. An undercut beneath the flat surface is available for insertion of a fork-like member to extract the shank portion from the base cast.

The two part dowel pin provides numerous benefits as were described in the aforementioned parent application. Specifically, it permits improved positioning, it provides for utilization of the dental model cast without interference by the cast and provides improved engagement between the two parts of the cast.

However, frequently the dental model cast must be manipulated and worked on while it is firmly held in place. Accordingly, it would be desirous to have the dental model cast able to be inserted into the base cast while it is being manipulated and worked on, and at the same time avoid the necessity of having a one-piece dowel pin which may have a tendency of becoming bent and damaged during continued insertion and removal from the base cast. Furthermore, the extension of the shank portion outwardly from the bottom of the base cast also may provide difficulty since it may be awkward to place the base cast on a surface and the exposed portions of the shank may also become bent or damaged.

SUMMARY OF THE INVENTION

Accordingly, it is an object of the present invention to provide a two-part pin arrangement for prosthodontic casts which avoids the disadvantages of the prior art.

Another object of the present invention is to provide a dowel pin for use between dental model casts and a base cast which is simple in construction, and economical to manufacture.

It is a further object of the present invention to provide a two-part dowel pin having a head portion which can be inserted into a dental model cast and a shank portion which can be inserted into a base cast, and wherein the head portion includes a collar which can enter into the base cast for temporary retention.

It is a further object of the present invention to provide a two-part dowel pin having a head portion which is inserted into the dental model cast and a shank portion which is inserted into a base cast and wherein the shank portion is contained completely within the base cast and does not extend outwardly therefrom.

Yet another object of the present invention is to provide a two-part dowel pin in conjunction with a tool for both threading and unthreading the shank portion to and from a head portion of the dowel pin, and possibly another tool for extracting the shank portion from the base cast.

It is a further object of the present invention to provide a two-part dowel pin having a head portion which is inserted into a dental model cast and a shank portion which is inserted into a base coat and wherein the head portion includes an axially extending externally threaded male member which is received within an internally threaded female member contained in the shank portion.

In order to achieve the above objects, the present invention includes a dowel pin for removably mounting a dental model cast relative to a base cast. The dowel pin comprises a head portion and a shank portion extending therefrom. The head portion is adapted to be fixedly secured in the dental model cast and the shank portion is adapted to be removably inserted into a complementary opening in the base cast. The two parts can be axially engaged and disengaged from each other. The head portion includes an externally threaded male member axially extending therefrom. A collar surrounds the base of the male member and has an outer diameter approximating the diameter of the shank portion so that it can enter into the opening of the base cast. The shank portion has an internally disposed, complementary thread which defines the female member for receiving the male member therein.

In an embodiment of the invention, at the opposing end of the shank portion there is provided a manipulating means in the form of a bayonet slot. A first tool is provided with an axially extending blade which can enter into the longitudinal portion of the bayonet slot and be utilized for both threading and unthreading the shank portion to and from the head portion. Preferably, a second tool having diametrically arranged pins laterally extending therefrom is insertable into the bayonet slot for removing the shank portion from the base cast.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENT

Figure 1:
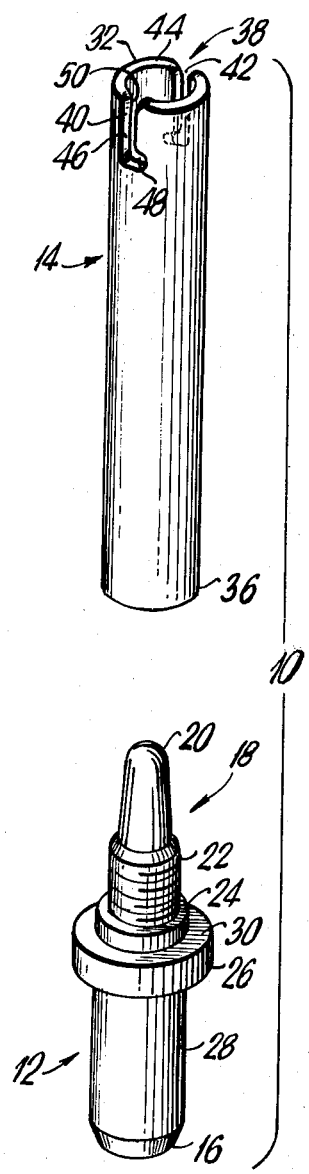
FIG. 1 is an exploded perspective view of the two-part dowel pin in accordance with the present invention.

Referring now to the drawings, in which the same reference numerals are utilized to designate similar or identical parts throughout, FIG. 1 shows the two-part dowel pin 10 of the present invention. The dowel pin 10 includes a head portion 12 and a shank portion 14. The head portion 12 has a chamfer 16 at one end of its body portion 28 and a tip section 18 having a reduced cross section, at the other end thereof. The tip section 18 includes a tapered pilot end 20 and an external threaded section 22 which is disposed inwardly from the pilot end 20. A collar 24 is located around the base of the externally threaded member 22. An outwardly extending peripheral flanged section 26 is formed intermediate the body portion 28 of the head portion 12 and the tip section 18. The outer face 30 of the flange is substantially flat.

The shank portion is a hollow, tubular member having an outer peripheral wall 32. An internal thread 34 is provided in the lower end 36 of the shank portion 14 which corresponds to the externally threaded portion 22 on the head portion 12.

Figure 2:
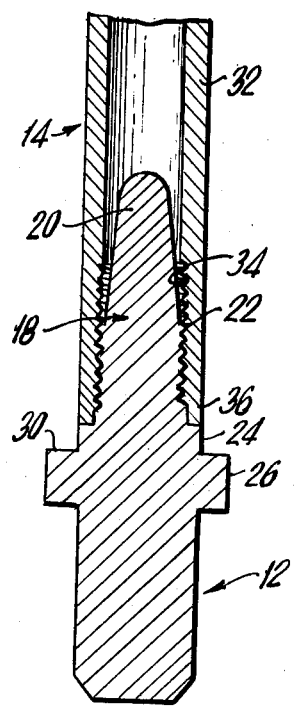
FIG. 2 is a fragmented cross sectional view showing the threaded engagement between the head and shank portions of the dowel pin.

Thus, as shown in FIG. 2, the pilot end 20 of the tip section 18 on the head portion 12 guides the tip section into the shank portion 14 and is received in the internally threaded end 36 as the threads 22 engage with the threads 34. Once the body of the shank portion 14 abuts against the collar 24 of the head portion 12, the two portions 12 and 14 are threadedly engaged as a unit.

The opposite end of the shank portion 14 is provided with a manipulating end shown generally at 38. The manipulating end includes a bayonet slot 40 in one side of the wall 32 with a corresponding diametrically opposed bayonet slot 42 formed in an opposed side of the outer wall 32. The bayonet slots extend from the free end 44 opposing the threaded end 36, and extend longitudinally along the side walls of the shank portion 14.

Figure 4:
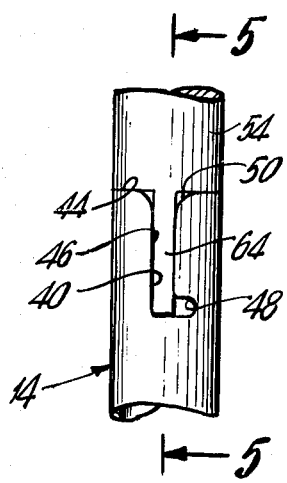
FIG. 4 is a fragmented side view showing the engagement between the tool and the shank portion.

As can be best seen in FIG. 4, each bayonet slot is L-shaped and includes an axially extending slot section 46 and a radially extending leg section 48. The upper portions of the walls of each slot section 46 are tapered so as to provide a wide mouth 50 at the free end 44 of the shank portion 14.

Figure 3:
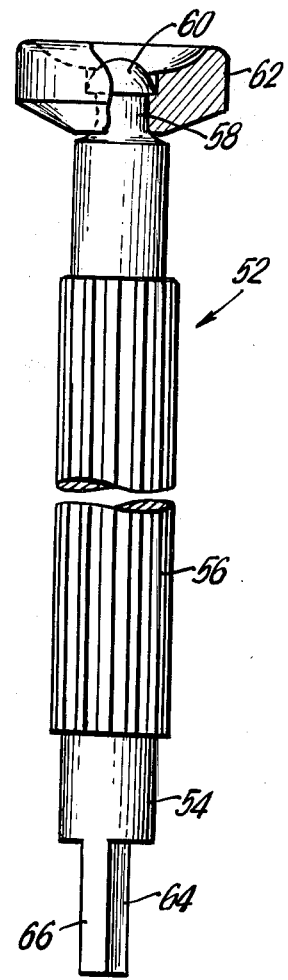
FIG. 3 is a fragmented perspective view, partly in section, of a tool for both threading and unthreading the shank portion to and from the head portion.

FIG. 3 shows a tool 52 for threading and unthreading the shank portion 14 to and from the head portion 12. The tool 52 is constructed from manual holding thereof and includes a cylindrical body member 54 which has a portion thereof knurled at 56 for finger gripping thereof. A pin 58 with an enlarged arcuate head 60 extends centrally outwardly from the top of the body member 54 for rotatably holding a finger positioner disc 62 thereon.

The opposite end of the body member 54 is provided with an axially extending blade 64 having a substantially rectangular shape with the outer edges 66 thereof being slightly curved as a continuation of the cylindrical body member 54.

Figure 5:
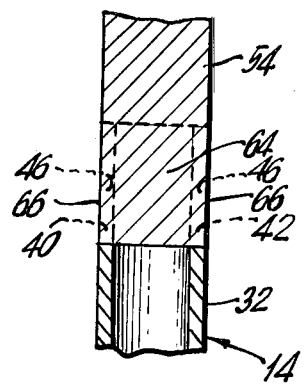
FIG. 5 is a fragmented sectional view taken along lines 5—5 of FIG. 4 and showing the engagement between the tool and the shank portion.

The blade 64 is configured to enter into the axially extending slot sections 46 of the bayonet slots 40, 42, as can best be seen in FIGS. 4 and 5. The wide mouths 50 of the slots aid in permitting the insertion of the blade into the slots. With the blade 64 inserted into the slots, the body member 54 may be rotated in a manner similar to a screwdriver entering into the slotted head of a screw. Thus, by using the tool 52, the shank portion 14 can be easily threaded onto and unthreaded from the head portion 12, the purpose of which will be more fully discussed hereinafter below.

Figure 6:
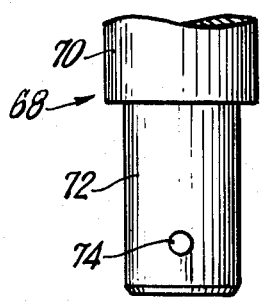
FIG. 6 is a fragmented side view of a second tool useful for extracting the shank portion from the base cast.
Figure 7:
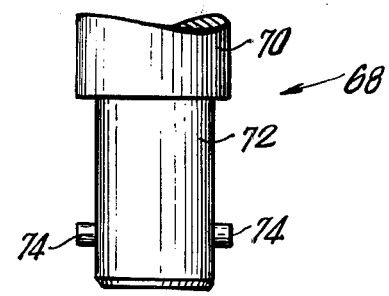
FIG. 7 is a fragmented side view taken 90° from the view shown in FIG. 6.
Figure 8:
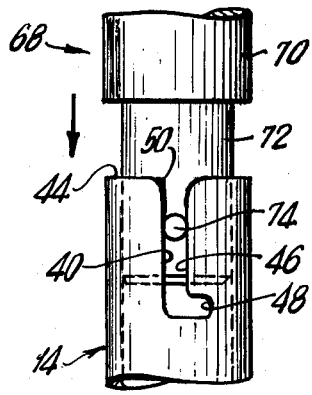
FIG. 8 is a fragmented side view showing the partial insertion of the tool shown in FIGS. 6 through 7 into the shank portion for removal thereof from the base cast.
Figure 9:
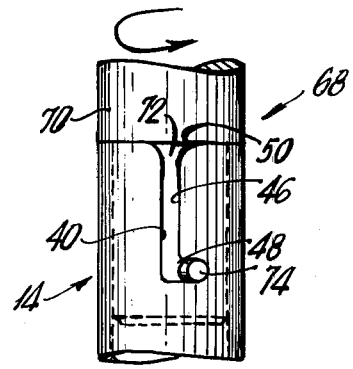
FIG. 9 is a view similar to that of FIG. 8 showing the full insertion of the tool for the removal of the shank portion from the base cast.

Referring now to FIGS. 6 and 7, there is shown a second tool 68 having a body portion 70 with an axially extending cylindrical member 72 having diametrical disposed pins 74 laterally extending therefrom. The outer diameter of the cylindrical member 72 proximates the inner diameter of the shank portion 14 so that the cylindrical member 72 can fit into the shank portion as the pins 74 enter the slot sections 46 of the bayonet slots 40, 42. As shown by the arrow in FIG. 8, the tool 68 is inserted with the pins 74 sliding down the slot section 46 of the slots until it reaches the bottom portions of the slots. The tool 68 is then rotated, as shown by the arrow in FIG. 9, so that the pins 74 engage within the leg sections 48 of the bayonet slots 40, 42. The pins 74 will then be held in place within the bayonet slots, and as the tool 68 is axially pulled in an upward direction, it will carry the shank portion 14 with it. Thus, the tool 68 can be utilized to extract the shank portion 14 from the base cast, the purpose of which will be more fully discussed hereinbelow.

It is noted, that the body portion 70 of the tool 68 can be made the same as the body member 54 of the tool 52, so that a full showing thereof is not thought necessary. It is further noted, that the tool 68 could also be used to both thread and unthread the shank portion 14 relative to the head portion 12, though the tool 52 is preferred.

Figure 10:
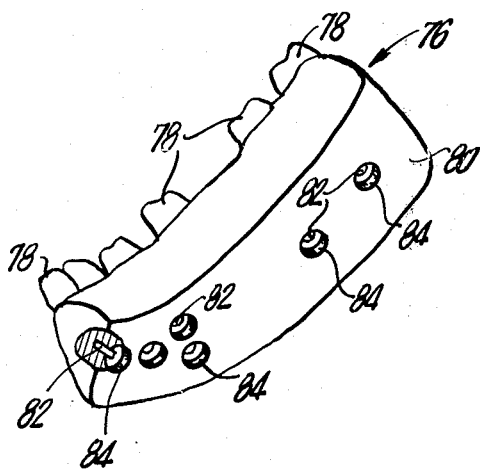
FIG. 10 is a perspective view, partly in section, of a dental model cast.

FIG. 10 shows a positive cast or a dental model cast 76 which is formed from an impression tray in accordance with techniques well known in the art. Dental model cast 76 is formed with tooth impressions 78 and one side thereof, where the opposite underside 80 is provided with a substantially flat surface. Accordingly, holes 82 are drilled into the flat underside 80 and are provided with countersinks 84. Preferably, there are two holes 82 for each anticipated segment which is to be cut from the dental model cast 76, as is described in the aforementioned U.S. Pat. No. 3,932,939, to which reference should be made for a fuller description thereof.

Figure 11:
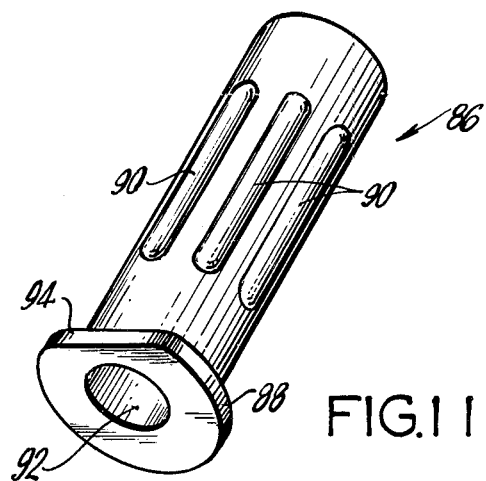
FIG. 11 is a perspective view of a sleeve member for receiving the shank portion therein.

FIG. 11 shows a tubular sleeve or bushing 86 which receives the shank portion 14. The sleeve 86 is provided with an annular shoulder 88 at one free end thereof which is substantially planar and extends in a radial direction. The body of the sleeve 86 is provided with elongated external ribs 90 which extend in a longitudinal direction, in the same direction as the opening 92 which extends longitudinally through the sleeve 86. Additionally, the annular shoulder 88 is provided with a cutaway edge portion 94. Both the ribs 90 and the cutaway edge portion 94 function to retain the sleeve 86 in the base cast, wherein the ribs 90 prevent the sleeve from being pulled out of the base cast, and also prevent rotation of the sleeve in the base cast. The cutaway edge portion 94 provides an additional feature to prevent rotation of the sleeve 86 in the base cast, where the formation of the base cast will be described hereinafter below.

Figure 12:
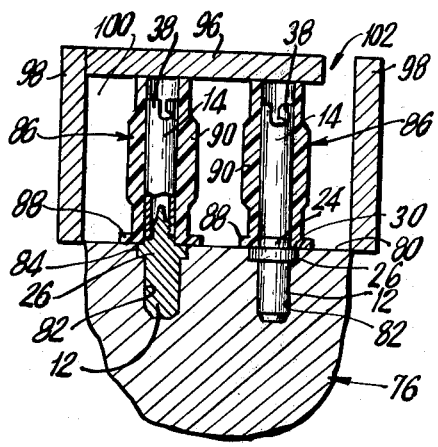
FIG. 12 is a cross sectional view of the dental model cast having dowel pins therein and provided with max sheets in preparation for the formation of the base cast.

As shown in FIG. 12, the first step in preparing the base cast is to fixedly secure the head portions 12 in the holes 82 in the flat surface 80 of the dental model cast 76, preferably by adhesive or cement means well known in the art. Accordingly, the peripheral flange 26 of the head portion 12 is received in the countersinks 84 so that the exposed end surface 30 of the peripheral flanges 26 is in flush alignment with the flat surface 80 of the dental model cast 76. After the securement of the head portion 12, the shank portion 14 is threadedly engaged therewith, such as by using the tool 52, and the sleeve 86 is positioned on the shank portion 14 so that the annular shoulder 88 is positioned adjacent to the flat surface 80 of the dental model cast 76 as shown in FIG. 12.

A wax sheet 96 is disposed over and rests against the opposite ends of the sleeve 86 to be substantially parallel to the flat surface 80 of the dental model cast 76. Preferably, the manipulating ends 38 extend inwardly from the wax sheet 96, as shown in FIG. 12, so as to be spaced from the wax and whereby it is completely contained within the sleeve 86. Further wax sheets 98 are disposed about the periphery of the flat surface 80 to form a dam or substantially vertical wall, which, together with the wax sheet 96, define a substantially closed space 100. Accordingly, the wax sheet 96 is selected to be somewhat smaller than the flat surface 80 to thereby provide at least one space or opening 102 to permit access to the interior of the space 100.

Figure 13:
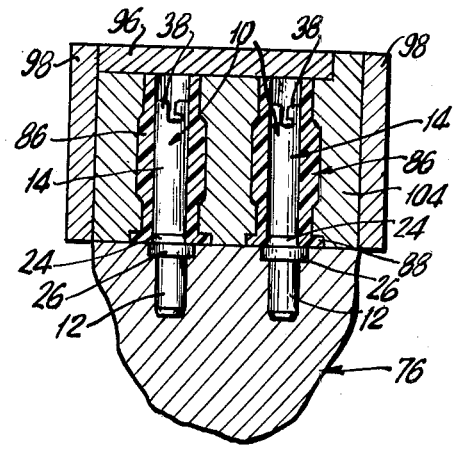
FIG. 13 is similar to FIG. 12 and shows a plaster base cast formed on the dental model cast.

With the above arrangements, a conventional plaster, or any other suitable material utilized for this purpose, can be poured into the space 100 through the access opening 102. Thus, as shown in FIG. 13, the sleeves 86 are embedded within the plaster which defines the base cast 104. It is noted, that the plaster does not physically come into contact with any of the dowel pins 10, so that the dowel pins 10 are free to slidably move or extend through the sleeves 86.

Figure 14:
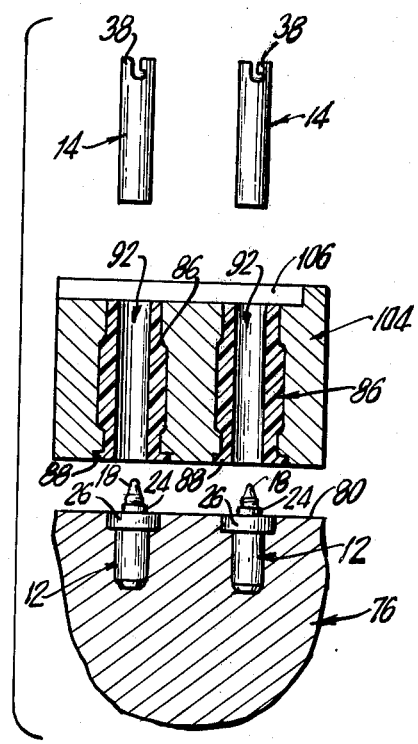
FIG. 14 is an exploded view, partly in section, showing the shank portions of the dowel pins removed from the base cast and separated from the head portions which are secured in the dental model cast.

After the plaster or base cast 104 has hardened, the wax sheets or walls 96, 98, are removed as shown in FIG. 14. To prevent any adhesion between the base cast 104 and the dental model cast 76, any suitable lubricant may be provided on the flat surface 80 prior to the pouring of the plaster. In this manner, the base cast 104 can be removed or separated from the dental model cast 76 without any great effort. It is noted, that the removal of the wax sheet 96 forms a recess 106 in the surface of the base cast 104.

The hardened base cast 104 can now be removed from the dental model cast 76 to provide the separated parts as shown in FIG. 14. The first step is to unthread the shank portion 14 from the head portion 12, using the tool 52, as was described above, whereby the tool 52 has easy access into the manipulating end 38 and can rotate the shank portion for unthreading thereof.

After the shank portion 14 is unthreaded, the shank portion 14 is preferably pulled out of the sleeve 86 which is secured in the base cast 104. This operation is achieved by means of the tool 68, as heretofore described. The tool 68 is inserted so that the pins 74 extend into the bayonet slots 40, 42. The tool 68 is twisted and then pulled, whereby the pins 74 are engaged in the leg sections 48 and pull the shank portion 14 from the sleeve 86, where the pins 74 are designed to fit in the opening 92 of the sleeve 86. The operation of extracting the shank portion 14 from the sleeve 86 can be performed before or after the dental model cast 76 is removed from the base cast 104.

Once the shank portions 14 are unthreaded, whether or not they are removed from the sleeve 86, the base cast 104 can easily be lifted off the dental model cast 76 where there is no connection therebetween. It is noted, that the head portions 12 remain secured in the dental model cast 76.

Figure 15:
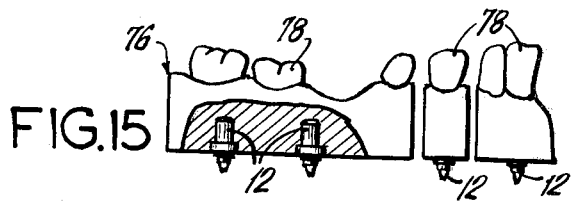
FIG. 15 is an elevational view, partly in section, showing the dental model cast cut into segments.

If desired, the dental model cast 76 may now be cut into segments, as shown in FIG. 15. Preferably, at least two head portions 12 are disposed in each segment for receiving associated shank portions 14, whereby two dowel pins 10 will hold and retain a segment on the base cast 104 in its original position so that the dentist can perform the required work thereon.

Figure 16:
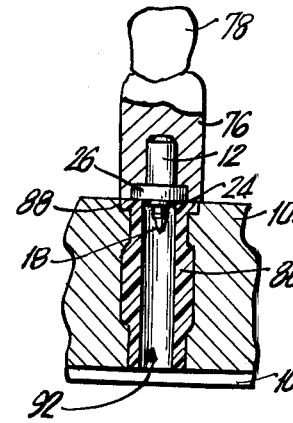
FIG. 16 is an elevational view, partly in section, showing the head portion temporarily retaining a segment of the dental model cast on the base cast.

According to the present invention, the segments of the dental model cast can be temporarily replaced onto the base cast 104 for manipulation and working on the teeth 78 contained in each segment. This is achieved as shown in FIG. 16 by means of the collar 24, it being noted that the shank portion 14 is not required at this stage. The outer diameter of the collar 24 proximates the opening in the sleeve 86. By means of the pilot end 20, for directing insertion into the sleeve 86, the segment of the dental model cast can be temporarily replaced with the collar 24 inserted into the opening 92 in the sleeve 86. This will temporarily retain the segments in place while they are being worked on. Additionally, when connecting the shank portion 14 to the head portion 12, it will be easier to first place the head portions in place by means of the pilot ends 20 serving as locating pins and the collars 24 temporarily holding the segments in place. The shank portions can then be pushed into place and threaded onto the head portions, using the tool 52 as mentioned above to thread the portions together.

Figure 17:
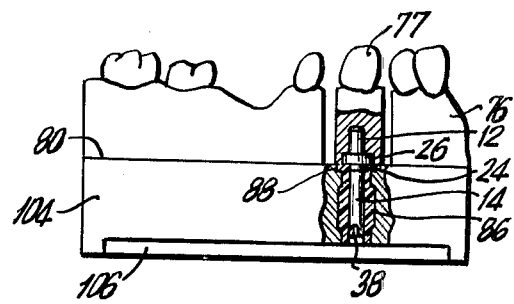
FIG. 17 is an elevational view, partly in section, showing the dowel pins positioning the segments of the dental model cast on the base cast.

Once the dental model cast 76 is cut into segments, these segments can be replaced and removed easily from the base cast 104 as shown in FIG. 17. Preferably, when replacing a segment, the head portions 12 are first placed into the openings 92 in the sleeves 86 and the shank portions 14 are again threaded into the head portions 12. The manipulating ends 38 of the shank portions and the tool 52 are utilized for the threaded connection. Alternately, first the shank portions 14 can be threaded onto the head portions 12, using the tool 52 if desired, and then the manipulating end 38 of the shank portion is guided into the sleeve 86 through the sleeve shoulder 88. The shank portions are then pushed into the sleeves 86 until the flat surface 80 of the segment abuts the base cast 104.

It is noted, that when the segment is again desired to be removed, the shank portion 14 is again unthreaded from the head portion 12 and the above mentioned process for removal thereof is repeated. It is further noted, that the shank portions 14 are interchangeable, whereby when broken, bent or otherwise damaged, the shank portions can be easily replaced. It should again be further noted that no significant force is exerted on any of the segments during removal thereof from the base cast 104, whereby the segments are merely lifted off the base cast 104 once the shank portions 14 are unthreaded.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dowel pin for removably mounting a dental model cast relative to a base cast, said dowel pin comprising a head portion and a shank portion extending therefrom, said head portion being adapted to be fixedly secured in the dental model cast and said shank portion being adapted to be removably insertable into a complementary opening in the base cast, said head portion including an externally threaded male member axially extending therefrom, a collar surrounding a base of said male member, said collar having an outer diameter proximating an outer diameter of said shank portion and being adapted to enter into the opening in the base cast, said shank portion having internally disposed complementary threads defining a female member for receiving said male member therein, said head portion and said shank portion being selectively engageable in axial alignment with each other and also being disengageable from each other, both when the dental model cast is mounted on the base cast as well as when the dental model cast and the base cast are separated, a free end of said male member being unthreaded to provide a pilot portion for guiding said male member into said female member.

2. A dowel pin as in claim 1, wherein said head portion includes an outwardly extending peripheral flange located adjacent to said collar on a side opposed from the male member, said flange being larger than said collar and being adapted to be positioned flush with an outer flat surface of the dental model cast.

3. A dowel pin as in claim 1, and further comprising manipulating means disposed at an end of said shank portion for moving said head and shank portions relative to each other, said shank portion end being opposite from said female member.

4. A dowel pin as in claim 3, wherein said manipulating means includes a slot longitudinally extending into said shank portion end for receiving a blade of a tool.

5. A dowel pin as in claim 4, wherein sidewall portions of said slot are tapered to provide a wide mouth at said shank portion end.

6. A dowel pin as in claim 3, in combination with a tool, said tool including means for moving said manipulating means to separate said shank portion from said head portion.

7. A dowel pin in combination with a tool as in claim 6, wherein said manipulating means includes an elongated slot at one end of said shank portion, and said tool means includes an elongated blade at one end of said tool for entering said slot.

8. A dowel pin in combination with a tool as in claim 6, wherein an opposite end of said tool is provided with a rotatably mounted finger positioner disk to aid in turning said tool, and a body portion of said tool being knurled for finger gripping thereof.

9. A dowel pin as in claim 1, wherein said shank portion is a hollow tubular member.

10. A dowel pin for removably mounting a dental model cast relative to a base cast, said dowel pin comprising a head portion and a shank portion extending therefrom, said head portion being adapted to be fixedly secured in the dental model cast and said shank portion being adapted to be removably insertable into a complementary opening in the base cast, said head portion including an externally threaded male member axially extending therefrom, a collar surrounding a base of said male member, said collar having an outer diameter proximating an outer diameter of said shank portion and being adapted to enter into the opening in the base cast, said shank portion having internally disposed complementary threads defining a female member for receiving said male member therein, said head portion and said shank portion being selectively engageable in axial alignment with each other and also being disengageable from each other, both when the dental model cast is mounted on the base cast as well as when the dental model cast and the base cast are separated, manipulating means disposed at an end of said shank portion for moving said head and shank portions relative to each other, said shank portion end being opposite from said female member, said manipulating means including a slot longitudinally extending into said shank portion end for receiving a blade of a tool, said slot being L-shaped to define a bayonet slot.

11. A dowel pin in combination with a tool for removably mounting a dental model cast relative to a base cast, said dowel pin comprising a head portion and a shank portion extending therefrom, said head portion being adapted to be fixedly secured in the dental model cast and said shank portion being adapted to be removably insertable into a complementary opening in the base cast, said head portion including an externally threaded male member axially extending therefrom, a collar surrounding a base of said male member, said collar having an outer diameter proximating an outer diameter of said shank portion and being adapted to enter into the opening in the base cast, said shank portion having internally disposed complementary threads defining a female member for receiving said male member therein, said head portion and said shank portion being selectively engageable in axial alignment with each other and also being disengageable from each other, both when the dental model cast is mounted on the base cast as well as when the dental model cast and the base cast are separated, manipulating means disposed at an end of said shank portion for moving said head and shank portions relative to each other, said shank portion end being opposite from said female member, said tool including means for moving said manipulating means to separate said shank portion from said head portion, said manipulating means including an elongated slot at one end of said shank portion, said tool means including an elongated blade at one end of said tool for entering said slot, said shank portion being tubular, said manipulating means including a bayonet slot provided at one end of said shank portion, said tool including a cylindrical body member having diametrically arranged pins extending therefrom, said cylindrical body member entering said shank portion with said pins engaging said bayonet slot.

* * * * *